(12) United States Patent
Lipshutz et al.

(10) Patent No.: US 8,095,323 B2
(45) Date of Patent: *Jan. 10, 2012

(54) POLYMORPHISM DETECTION

(75) Inventors: Robert J. Lipshutz, Palo Alto, CA (US); Ronald J. Sapolsky, Mountain View, CA (US); Ghassan Ghandour, Atherton, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/692,729

(22) Filed: Jan. 25, 2010

(65) Prior Publication Data

US 2010/0286924 A1    Nov. 11, 2010

Related U.S. Application Data

(63) Continuation of application No. 11/675,980, filed on Feb. 16, 2007, now Pat. No. 7,674,587, which is a continuation of application No. 11/247,053, filed on Oct. 11, 2005, now abandoned, which is a continuation of application No. 10/607,829, filed on Jun. 27, 2003, now Pat. No. 6,953,663, which is a continuation of application No. 09/939,119, filed on Aug. 24, 2001, now Pat. No. 6,586,186, which is a continuation of application No. 08/853,370, filed on May 8, 1997, now Pat. No. 6,300,063, which is a continuation-in-part of application No. 08/563,762, filed on Nov. 29, 1995, now Pat. No. 5,858,659.

(60) Provisional application No. 60/017,260, filed on May 10, 1996.

(51) Int. Cl.
*G01N 33/48* (2006.01)
*G01N 33/50* (2006.01)
*G01N 31/00* (2006.01)
*C12Q 1/68* (2006.01)

(52) U.S. Cl. ............. 702/20; 702/19; 702/22; 435/6.11; 435/6.1

(58) Field of Classification Search ................... None
See application file for complete search history.

(56) References Cited

U.S. PATENT DOCUMENTS 5,002,867 A    3/1991    Macevicz
(Continued)

FOREIGN PATENT DOCUMENTS

CA    2036946    10/1991
(Continued)

OTHER PUBLICATIONS

Southern et al. Analyzing and comparing nucleic acid sequences by hybridization of arrays of oligonucleotides: Evaluation using experimental models. Genomics, 1992, vol. 13, pp. 1008-1017.*

(Continued)

*Primary Examiner* — Russell S Negin
(74) *Attorney, Agent, or Firm* — Sandra E. Wells

(57) ABSTRACT

The present invention generally provides a rapid efficient method for analyzing polymorphic or biallelic markers, and arrays for carrying out these analyses. In general, the methods of the present invention employ arrays of oligonucleotide probes that are complementary to target nucleic acids which correspond to the marker sequences of an individual. The probes are typically arranged in detection blocks, each block being capable of discriminating the three genotypes for a given marker, i.e., the heterozygote or either of the two homozygotes. The method allows for rapid, automatable analysis of genetic linkage to even complex polygenic traits.

4 Claims, 10 Drawing Sheets

U.S. PATENT DOCUMENTS

| | | |
|---|---|---|
| 5,089,386 A | 2/1992 | Stackebrandt et al. |
| 5,143,854 A | 9/1992 | Pirrung et al. |
| 5,202,231 A | 4/1993 | Drmanac et al. |
| 5,242,974 A | 9/1993 | Holmes |
| 5,252,743 A | 10/1993 | Barrett et al. |
| 5,264,565 A | 11/1993 | England et al. |
| 5,270,170 A | 12/1993 | Schatz et al. |
| 5,302,707 A | 4/1994 | Campbell et al. |
| 5,324,633 A | 6/1994 | Fodor et al. |
| 5,338,665 A | 8/1994 | Schatz et al. |
| 5,359,115 A | 10/1994 | Campbell et al. |
| 5,362,899 A | 11/1994 | Campbell |
| 5,384,261 A | 1/1995 | Winkler et al. |
| 5,405,783 A | 4/1995 | Pirrung et al. |
| 5,412,087 A | 5/1995 | McGall et al. |
| 5,420,328 A | 5/1995 | Campbell |
| 5,424,186 A | 6/1995 | Fodor et al. |
| 5,427,908 A | 6/1995 | Dower et al. |
| 5,432,018 A | 7/1995 | Dower et al. |
| 5,445,934 A | 8/1995 | Fodor et al. |
| 5,451,683 A | 9/1995 | Barrett et al. |
| 5,482,867 A | 1/1996 | Barrett et al. |
| 5,489,678 A | 2/1996 | Fodor et al. |
| 5,491,074 A | 2/1996 | Aldwin et al. |
| 5,498,530 A | 3/1996 | Schatz et al. |
| 5,503,805 A | 4/1996 | Sugarman et al. |
| 5,510,270 A | 4/1996 | Fodor et al. |
| 5,527,670 A | 6/1996 | Stanley |
| 5,527,681 A | 6/1996 | Holmes |
| 5,541,061 A | 7/1996 | Fodor et al. |
| 5,545,531 A | 8/1996 | Rava et al. |
| 5,547,839 A | 8/1996 | Dower et al. |
| 5,550,215 A | 8/1996 | Holmes |
| 5,556,752 A | 9/1996 | Lockhart et al. |
| 5,571,639 A | 11/1996 | Hubbell et al. |
| 5,578,832 A | 11/1996 | Trulson et al. |
| 5,593,839 A | 1/1997 | Hubbell et al. |
| 5,599,695 A | 2/1997 | Pease et al. |
| 5,607,832 A | 3/1997 | Stanley et al. |
| 5,624,711 A | 4/1997 | Sundberg et al. |
| 5,631,734 A | 5/1997 | Stern et al. |
| 5,690,894 A | 11/1997 | Pinkel et al. |
| 5,795,716 A | 8/1998 | Chee |
| 5,837,832 A | 11/1998 | Chee et al. |
| 5,858,659 A | 1/1999 | Sapolsky et al. |
| 6,027,880 A | 2/2000 | Cronin et al. |
| 6,040,138 A | 3/2000 | Lockhart et al. |
| 6,300,063 B1 | 10/2001 | Lipshutz et al. |
| 6,309,823 B1 | 10/2001 | Cronin et al. |
| 6,586,186 B2 | 7/2003 | Lipshutz et al. |
| 6,953,663 B1 | 10/2005 | Lipshutz et al. |
| 2001/0053519 A1 | 12/2001 | Fodor et al. |

FOREIGN PATENT DOCUMENTS

| | | |
|---|---|---|
| WO | WO 89/10977 | 11/1989 |
| WO | WO 90/15070 | 12/1990 |
| WO | WO 91/07087 | 5/1991 |
| WO | WO 92/04470 | 3/1992 |
| WO | WO 92/10092 | 6/1992 |
| WO | WO 92/10588 | 6/1992 |
| WO | WO 93/09668 | 5/1993 |
| WO | WO 93/10161 | 5/1993 |
| WO | WO 93/15224 | 8/1993 |
| WO | WO 93/22694 | 11/1993 |
| WO | WO 94/10128 | 5/1994 |
| WO | WO 94/28173 | 12/1994 |
| WO | WO 95/00530 | 1/1995 |
| WO | WO 95/11995 | 5/1995 |
| WO | WO 95/22058 | 8/1995 |
| WO | WO 95/25177 | 9/1995 |
| WO | WO 95/33846 | 12/1995 |
| WO | WO 97/10365 | 3/1997 |
| WO | WO 97/12063 | 4/1997 |
| WO | WO 97/23357 | 7/1997 |
| WO | WO 97/27317 | 7/1997 |
| WO | WO 97/29212 | 8/1997 |

OTHER PUBLICATIONS

Green DM. A Basic computer program for calculating indicies of genetic distance and similarity. The Journal of Heredity, 1979, vol. 40, pp. 429-430.*

Wada et al. Codon usage tabulated from the GenBank genetic sequence data. Nucleic Acids Research, supplement of vol. 20, 1992, pp. 2111-2118.*

Wu M. The Architecture of eNVy, a non-volatile, main memory storage system. Rice University Masters Dissertation, 1994, 51 pages.*

Brenner, S. et al. "DNA fingerprinting by sampled sequencing," Proc.Natl.Acad.Sci.U.S.A, vol. 86, Nov. 1989, pp. 8902-8906.

Fodor, S. P. et al. "Light-directed, spatially addressable parallel chemical synthesis," Science, vol. 251, Feb. 15, 1991, pp. 767-773.

Guo, Z. et al. "Direct fluorescence analysis of genetic polymorphisms by hybridization with oligonucleotide arrays on glass supports," Nucleic Acids Res., vol. 22, Dec. 11, 1994, pp. 5456-5465.

Hoheisel, J. D.,"Application of hybridization techniques to genome mapping and sequencing," Trends Genet., vol. 10, Mar. 1994, pp. 79-83.

Hotelling, H.,"Analysis of a complex of statistical variables into principal components," Journal of Educational Psychology,vol. 26, Sep. 1933, pp. 417-441.

Hotelling, H.,"Analysis of a complex of statistical variables into principal components," Journal of Educational Psychology,vol. 26, Oct. 1933, pp. 498-520.

Hotelling, Harold, Simplified calculation of principal components, Psychometrika, Mar. 1936, 1(1): 27-35.

Lipshutz, R. J. et al. "Using oligonucleotide probe arrays to access genetic diversity," Biotechniques, vol. 19, Sep. 1995, pp. 442-447.

Pearson,K."On lines and planes of closest fit to systems of points in space," In the London, Edinburgh, and Dublin Philosophical Magazine and Journal of Science, vol. 2, Sixth Series, Jul.-Dec. 1901, pp. 559-572.

Pease, A. C.,"Light-Generated Oligonucleotide Arrays for Rapid DNA Sequence Analysis," Proc National Acad Science, vol. 91, 1994, pp. 5022-5026.

Sapolsky, R. J. et al. "Mapping genomic library clones using oligonucleotide arrays," Genomics, 33, May 1, 1996, pp. 445-456.

Smith, D.R.,"Ligation-mediated PCR of restriction fragments from large DNA molecules" PCR Methods and Applications vol. 2, pp. 21-27 (1992).

Southern, E. M. et al. "Analyzing and comparing nucleic acid sequences by hybridization to arrays of oligonucleotides: evaluation using experimental models," Genomics, 13, Aug. 1992, pp. 1008-1017.

Szybalski, W. et al. "Class-IIS restriction enzymes—a review," Gene, vol. 100, Apr. 1991, pp. 13-26.

Szybalski, W.,"Universal restriction endonucleases: designing novel cleavage specificities by combining adapter oligodeoxynucleotide and enzyme moieties," Gene,vol. 40, 1985, pp. 169-173.

Unrau, P. et al. "Non-cloning amplification of specific DNA fragments from whole genomic DNA digests using DNA 'indexers'," Gene, vol. 145, Aug. 5, 1994, pp. 163-169.

Matthews, Jayne A. et al. "Analytical strategies for the use of DNA probes," Analytical Biochemistry, vol. 169, Feb. 15, 1988, pp. 1-25.

Lipshutz, et al, "Using oligonucleotide probe arrays to access genitc diversity," Biotechniques, vol. 19, No. 3, pp. 442-447 (1995).

* cited by examiner

DB = "DECIBELS" = 10 × LOG (DETECTION RATIO)

DETECTION RATIO = $\frac{\text{A PERFECT MATCH} - \text{A MISMATCHES}}{\text{B PERFECT MATCH} - \text{B MISMATCHES}}$ C = SIGNIFICANCE CHECK = $\frac{\text{MAX (A OR B PERFECT MATCH)}}{\sigma \text{ (A OR B MISMATCHES)}} > 2$ P = PATTERN MATCHING = $\frac{\text{MEAN [MAX (A OR B PERFECT MATCHES)]}}{\text{MEAN [MAX(A OR B MISMATCHES)]}} > 1.2$

PREDICTED PATTERNS

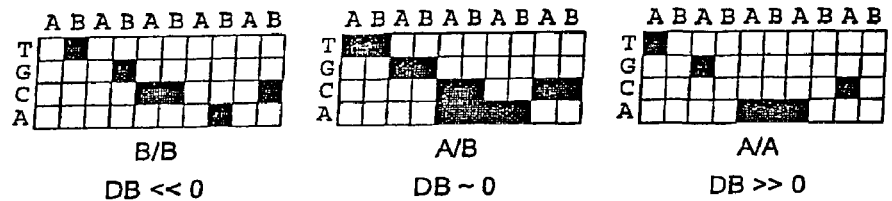

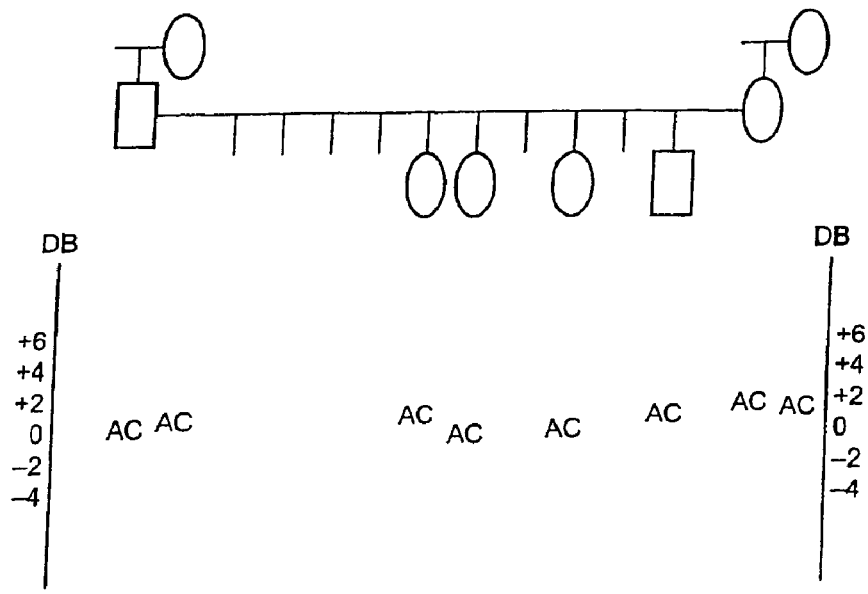

FIG 13

POLYMORPHISM DETECTION

This application is a continuation of Ser. No. 11/675,980, filed on Feb. 16, 2007, which is a continuation of Ser. No. 11/247,053, filed on Oct. 11, 2005, which is a continuation of Ser. No. 10/607,829, filed Jun. 27, 2003, now U.S. Pat. No. 6,953,663, which a continuation of Ser. No. 09/939,119, filed Aug. 24, 2001, now U.S. Pat. No. 6,586,186, which is a continuation of Ser. No. 08/853,370, filed May 8, 1997, now U.S. Pat. No. 6,300,063, which is a continuation-in-part of Ser. No. 08/563,762, filed Nov. 29, 1995, now U.S. Pat. No. 5,858,659 and claims the benefit of U.S. provisional application 60/017,260, filed May 10, 1996. Each of these applications is incorporated herein by reference in its entirety for all purposes.

BACKGROUND OF THE INVENTION

The relationship between structure and function of macromolecules is of fundamental importance in the understanding of biological systems. These relationships are important to understanding, for example, the functions of enzymes, structural proteins and signaling proteins, ways in which cells communicate with each other, as well as mechanisms of cellular control and metabolic feedback.

Genetic information is critical in continuation of life processes. Life is substantially informationally based and its genetic content controls the growth and reproduction of the organism and its complements. The amino acid sequences of polypeptides, which are critical features of all living systems, are encoded by the genetic material of the cell. Further, the properties of these polypeptides, e.g., as enzymes, functional proteins, and structural proteins, are determined by the sequence of amino acids which make them up. As structure and function are integrally related, many biological functions may be explained by elucidating the underlying structural features which provide those functions, and these structures are determined by the underlying genetic information in the form of polynucleotide sequences. Further, in addition to encoding polypeptides, polynucleotide sequences also can be involved in control and regulation of gene expression. It therefore follows that the determination of the make-up of this genetic information has achieved significant scientific importance.

As a specific example, diagnosis and treatment of a variety of disorders may often be accomplished through identification and/or manipulation of the genetic material which encodes for specific disease associated traits. In order to accomplish this, however, one must first identify a correlation between a particular gene and a particular trait. This is generally accomplished by providing a genetic linkage map through which one identifies a set of genetic markers that follow a particular trait. These markers can identify the location of the gene encoding for that trait within the genome, eventually leading to the identification of the gene. Once the gene is identified, methods of treating the disorder that result from that gene, i.e., as a result of overexpression, constitutive expression, mutation, underexpression, etc., can be more easily developed.

One class of genetic markers includes variants in the genetic code termed "polymorphisms." In the course of evolution, the genome of a species can collect a number of variations in individual bases. These single base changes are termed single-base polymorphisms. Polymorphisms may also exist as stretches of repeating sequences that vary as to the length of the repeat from individual to individual. Where these variations are recurring, i.e., exist in a significant percentage of a population, they can be readily used as markers linked to genes involved in mono- and polygenic traits. In the human genome, single-base polymorphisms occur roughly once per 300 bp. Though many of these variant bases appear too infrequently among the allele population for use as genetic markers (i e, $\leq 1\%$), useful polymorphisms (e.g., those occurring in 20 to 50% of the allele population) can be found approximately once per kilobase. Accordingly, in a human genome of approximately 3 Gb, one would expect to find approximately 3,000,000 of these "useful" polymorphisms.

The use of polymorphisms as genetic linkage markers is thus of critical importance in locating, identifying and characterizing the genes which are responsible for specific traits. In particular, such mapping techniques allow for the identification of genes responsible for a variety of disease or disorder-related traits which may be used in the diagnosis and or eventual treatment of those disorders. Given the size of the human genome, as well as those of other mammals, it would generally be desirable to provide methods of rapidly identifying and screening for polymorphic genetic markers. The present invention meets these and other needs.

SUMMARY OF THE INVENTION

One aspect of the invention is an array of oligonucleotide probes for detecting a polymorphism in a target nucleic acid sequence using Principal Component Analysis, said array comprising at least one detection block of probes, said detection block including a first group of probes that are complementary to said target nucleic acid sequence except that the group of probes includes all possible monosubstitutions of positions in said sequence that are within n bases of a base in said sequence that is complementary to said polymorphism, wherein n is from 0 to 5, and a second and third group of probes complementary to marker-specific regions upstream and downstream of the target nucleic acid sequence, wherein the third group of probes differs from the second set of probes at single bases corresponding to known mismatch positions.

A further aspect of the invention is a method of identifying whether a target nucleic acid sequence includes a polymorphic variant using principal component analysis, comprising hybridizing said target nucleic acid sequence to said array comprising at least one detection block of probes, said detection block including a first group of probes that are complementary to said target nucleic acid sequence except that the group of probes includes all possible monosubstitutions of positions in said sequence that are within n bases of a base in said sequence that is complementary to said polymorphism, wherein n is from 0 to 5, and a second and third group of probes complementary to marker-specific regions upstream and downstream of the target nucleic acid sequence, wherein the third group of probes differs from the second set of probes at single bases corresponding to known mismatch positions, and determining hybridization intensities of the target nucleic acid and the marker-specific regions to identify said polymorphic variant. In one embodiment of the invention, the step of determining comprises:

a) calculating the control difference between the average of the hybridization intensities of the second group of probes, the hybridization intensities comprising control perfect matches (PM), minus the average of the hybridization intensities, the hybridization intensities comprising control single-base mismatches (MM), b) calculating the possible perfect match intensity and a heteromismatch intensity from the hybridization intensities for each position of monosubstitutions of the first group of probes, c) calculating the difference between the possible perfect match intensity and the heteromismatch intensity for each position of monosubstitutions of the first group of probes, d) calculating a normalized difference (ND) by dividing the difference of step (c) by the control difference, and e) using principal component analysis, identifying a polymorphism by comparing normalized differences between individuals in a population.

BRIEF DESCRIPTION OF THE DRAWINGS

FIG. 2B also shows the triplet layout of detection blocks for the polymorphism employing 20-mer oligonucleotide probes having substitutions 7, 10 and 13 bp from the 3' end of the probe (AACCAANCTCG GGAGTAGAG, SEQ ID NO: 2; CGGAACCAANCTCGGGAGTA, SEQ ID NO: 3; CGACGGAACCAANCTCGGGA. SEQ ID NO: 4). The probes present in the shaded portions of each detection block are shown adjacent to each detection block.

FIG. 12 shows the algorithms used for identifying genotypes, using the methods of the present invention.

FIG. 13 shows the DB scores of one marker plotted along with the genotypes determined by standard sequencing. Approximately 220 biallelic markers were assayed together for each individual for a sixteen member family.

DETAILED DESCRIPTION OF THE INVENTION

I. General

The present invention generally provides rapid and efficient methods for screening samples of genomic material for polymorphisms, and arrays specifically designed for carrying out these analyses. In particular, the present invention relates to the identification and screening of single base polymorphisms in a sample. In general, the methods of the present invention employ arrays of oligonucleotide probes that are complementary to target nucleic acid sequence segments from an individual (e.g., a human or other mammal) which target sequences include specific identified polymorphisms, or "polymorphic markers." The probes are typically arranged in detection blocks, each block being capable of discriminating the three genotypes for a given marker, e.g., the heterozygote or either of the two homozygotes. The method allows for rapid, automatable analysis of genetic linkage to even complex polygenic traits.

Oligonucleotide arrays typically comprise a plurality of different oligonucleotide probes that are coupled to a surface of a substrate in different known locations. These oligonucleotide arrays, also described as "Genechips™," have been generally described in the art, for example, U.S. Pat. No. 5,143,854 and PCT patent publication Nos. WO 90/15070 and 92/10092. These arrays may generally be produced using mechanical synthesis methods or light directed synthesis methods which incorporate a combination of photolithographic methods and solid phase oligonucleotide synthesis methods. See Fodor et al, *Science,* 251 767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186, each of which is hereby incorporated herein by reference. Techniques for the synthesis of these arrays using mechanical synthesis methods are described in, e.g., U.S. Pat. No. 5,384,261, incorporated herein by reference in its entirety for all purposes.

Figure 1:
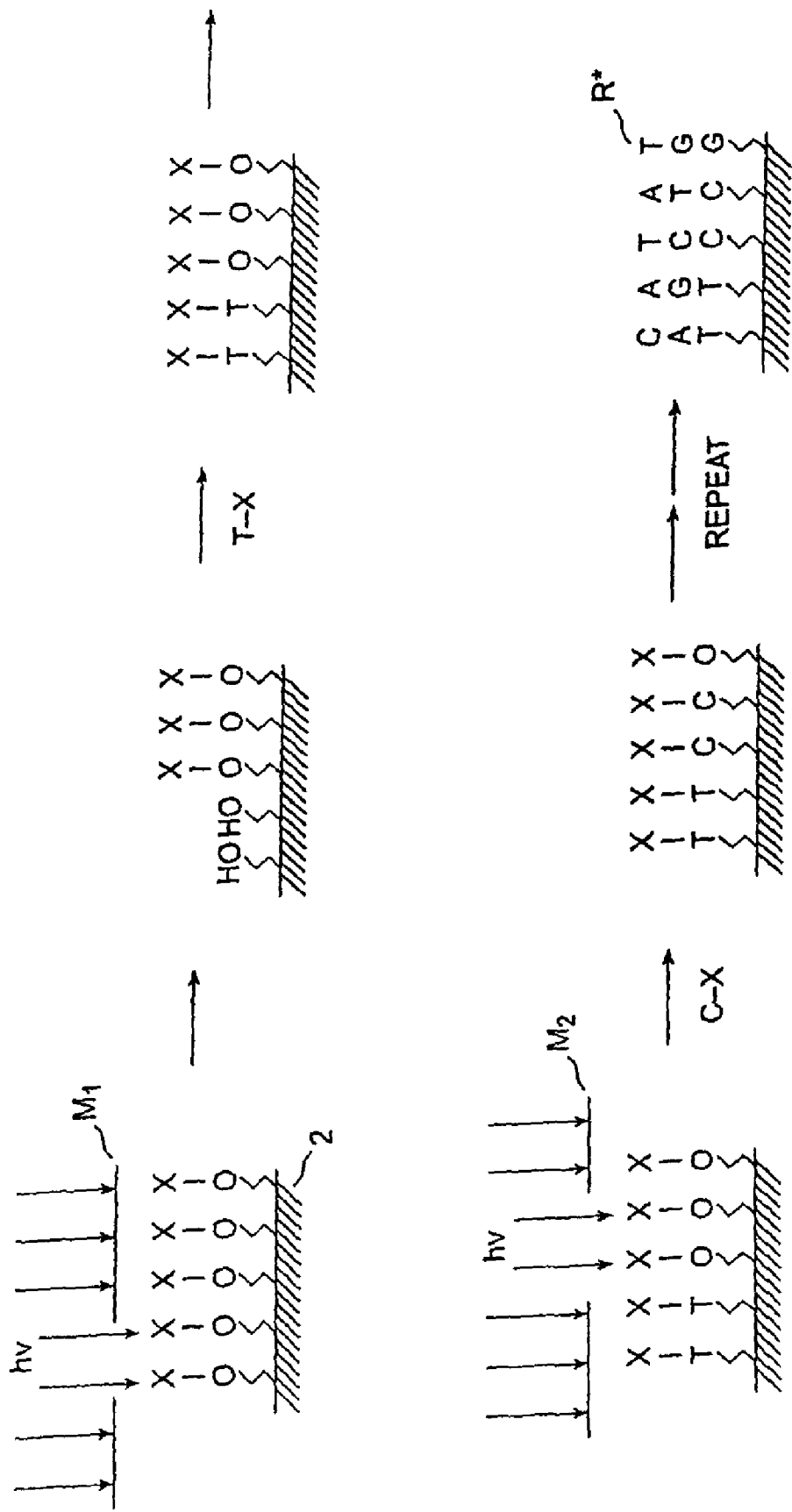
FIG. 1 shows a schematic illustration of light-directed synthesis of oligonucleotide arrays.

The basic strategy for light directed synthesis of oligonucleotides on a VLSIPS™ Array is outlined in FIG. 1. The surface of a substrate or solid support, modified with photosensitive protecting groups (X) is illuminated through a photolithographic mask, yielding reactive hydroxyl groups in the illuminated regions. A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light. Following capping and oxidation, the substrate is rinsed and the surface is illuminated through a second mask, to expose additional hydroxyl groups for coupling A second selected nucleotide (e.g., 5'-protected, 3'-O-phosphoramidite-activated deoxynucleoside) is presented to the surface. The selective deprotection and coupling cycles are repeated until the desired set of products is obtained Pease et al., *Proc. Natl Acad Sci.* (1994) 91 5022-5026. Since photolithography is used, the process can be readily miniaturized to generate high density arrays of oligonucleotide probes. Furthermore, the sequence of the oligonucleotides at each site is known.

II. Identification of Polymorphisms

The methods and arrays of the present invention primarily find use in the identification of so-called "useful" (i.e., those that are present in approximately 20 % or more of the allele population). The present invention also relates to the detection or screening of specific variants of previously identified polymorphisms. A wide variety of methods can be used to identify specific polymorphisms. For example, repeated sequencing of genomic material from large numbers of individuals, although extremely time consuming, can be used to identify such polymorphisms. Alternatively, ligation methods may be used, where a probe having an overhang of defined sequence is ligated to a target nucleotide sequence derived from a number of individuals. Differences in the ability of the probe to ligate to the target can reflect polymorphisms within the sequence. Similarly, restriction patterns generated from treating a target nucleic acid with a prescribed restriction enzyme or set of restriction enzymes can be used to identify polymorphisms. Specifically, a polymorphism may result in the presence of a restriction site in one variant but not in another. This yields a difference in restriction patterns for the two variants, and thereby identifies a polymorphism. In a related method, U.S. patent application Ser. No. 08/485,606, filed Jun. 7, 1995 describes a method of identifying polymorphisms using type-IIs endonucleases to capture ambiguous base sequences adjacent the restriction sites, and characterizing the captured sequences on oligonucleotide arrays. The patterns of these captured sequences are compared from various individuals, the differences being indicative of potential polymorphisms.

In a preferred aspect, the identification of polymorphisms takes into account the assumption that a useful polymorphism (i.e., one that occurs in 20 to 50% of the allele population) occurs approximately once per 1 KB in a given genome. In particular, random sequences of a genome, e.g., random 1 kb sequences of the human genome such as expressed sequence tags or "ESTs", can be sequenced from a limited number of individuals. When a variant base is detected with sufficient frequency, it is designated a "useful" polymorphism. In practice, the method generally analyzes the same 1 KB sequence from a small number of unrelated individuals, i.e., from 3 to 5 (6 to 10 alleles). Where a variant sequence is identified, it is then compared to a separate pool of material from unrelated individuals (i.e., 10 unrelated individuals). Where the variant sequence identified from the first set of individuals is detectable in the pool of the second set, it is assumed to exist at a sufficiently high frequency, i.e., at least about 20 % of the allele population, thereby qualifying as a useful marker for genetic linkage analysis.

III. Screening Polymorphisms

Screening polymorphisms in samples of genomic material according to the methods of the present invention, is generally carried out using arrays of oligonucleotide probes. These arrays may generally be "tiled" for a large number of specific polymorphism. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are discussed in detail in Published PCT Application No. WO 95/11995, incorporated herein by reference in its entirety for all purposes. By "target sequence" is meant a sequence which has been identified as containing a polymorphism, and more particularly, a single-base polymorphism, also referred to as a "biallelic base." It will be understood that the term "target sequence" is intended to encompass the various forms present in a particular sample of genomic material, i.e., both alleles in a diploid genome.

In a particular aspect, arrays are tiled for a number of specific, identified polymorphic marker sequences. In particular, the array is tiled to include a number of detection blocks, each detection block being specific for a specific polymorphic marker or set of polymorphic markers. For example, a detection block may be tiled to include a number of probes which span the sequence segment that includes a specific polymorphism. To ensure probes that are complementary to each variant, the probes are synthesized in pairs differing at the biallelic base.

Figure 3:
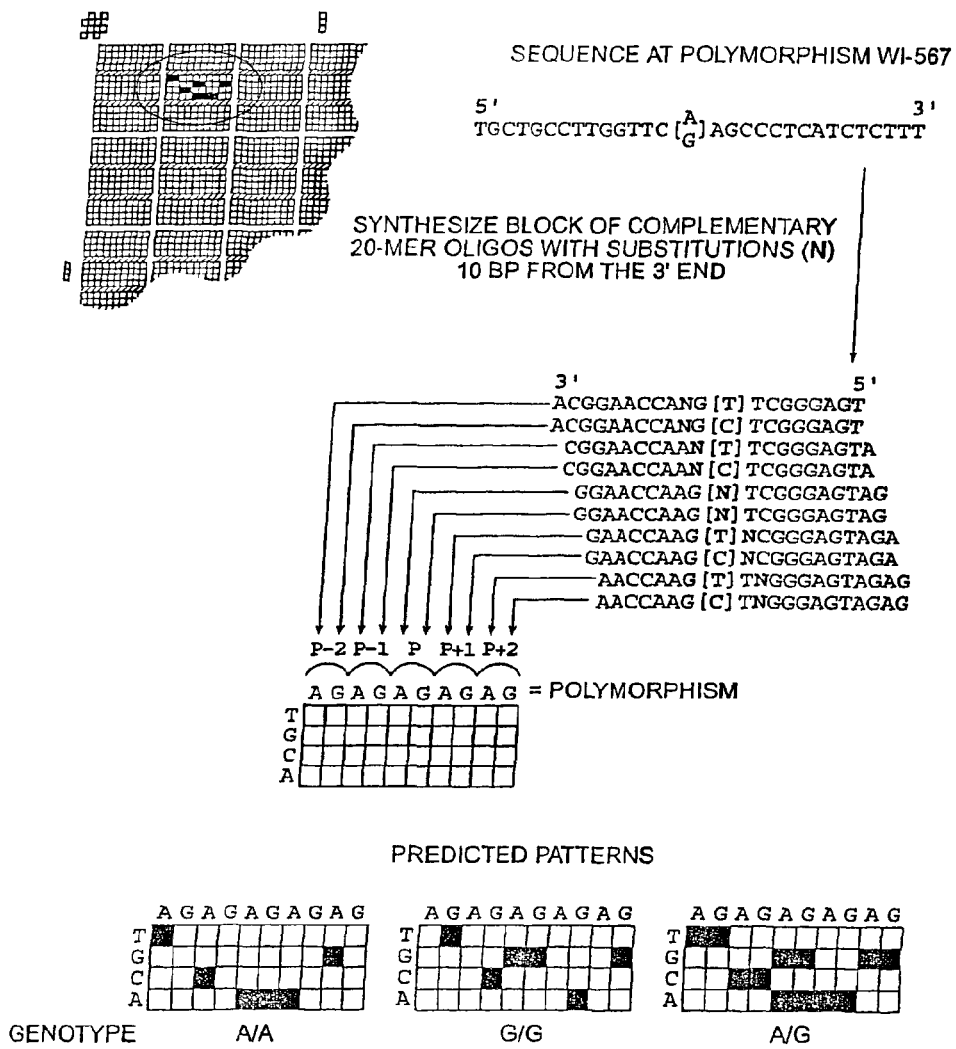
FIG. 3 illustrates a tiling strategy for a polymorphism denoted WI-567, and having the sequence 5'-TGCTGCCT-TGGTTC[A/G]AGCCCTCATCTCTTT-3' (TGCTGCCT-TGGTTCRAGCCCTCATCTCTTT, SEQ ID NO: 1). A detection block specific for the WI-567 polymorphism is shown with the probe sequences tiled therein listed above (ACGGAACCANGTTCGGGAGT, SEQ ID NO: 5; ACG-GAACCANGC TCGGGAGT, SEQ ID NO: 6; CGGAAC-CAANTTCGGGAGTA, SEQ ID NO: 7; CGGAAC-CAANCTCGGGAGTA, SEQ ID NO: 8; GGAACCAAGNTCGGGAGTA G; SEQ ID NO: 9; GAAC-CAAGTNCGGGAGTAGA. SEQ ID NO: 10; GAACCAAG CNCGGGAGTAGA, SEQ ID NO: 11; AACCAAGTTNGG-GAGTAGAG, SEQ ID NO: 12; AACCAAGCTNGGGAG-TAGAG, SEQ ID NO: 13). Predicted patterns for both homozygous forms and the heterozygous form are shown at the bottom.
Figure 4:
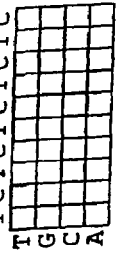
FIG. 4 shows a schematic representation of a detection block specific for the polymorphism denoted WI-1959 having the sequence 5'-ACCAAAAATCAGTC[T/C]GGGTAACT-GAGAGTG-3' (ACCAAAAATCAGTCYGGGTAACT-GAGAGTG, SEQ ID NO:14) with the polymorphism indicated by the brackets. A fluorescent scan of hybridization of the heterozygous and both homozygous forms are shown in the center, with the predicted hybridization pattern for each being indicated below.
Figure 4:
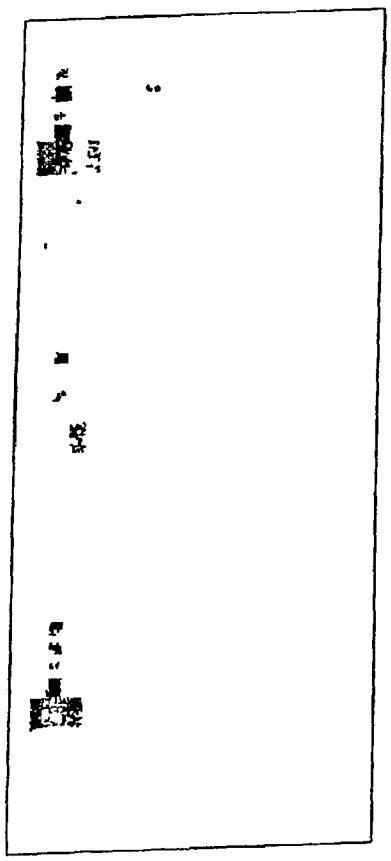

In addition to the probes differing at the biallelic bases, monosubstituted probes are also generally tiled within the detection block. These monosubstituted probes have bases at and up to a certain number of bases in either direction from the polymorphism, substituted with the remaining nucleotides (selected from A, T, G, C or U). Typically, the probes in a tiled detection block will include substitutions of the sequence positions up to and including those that are 5 bases away from the base that corresponds to the polymorphism. Preferably, bases up to and including those in positions 2 bases from the polymorphism will be substituted. The monosubstituted probes provide internal controls for the tiled array, to distinguish actual hybridization from artifactual cross-hybridization. An example of this preferred substitution pattern is shown in FIG. 3.

Figure 2A:
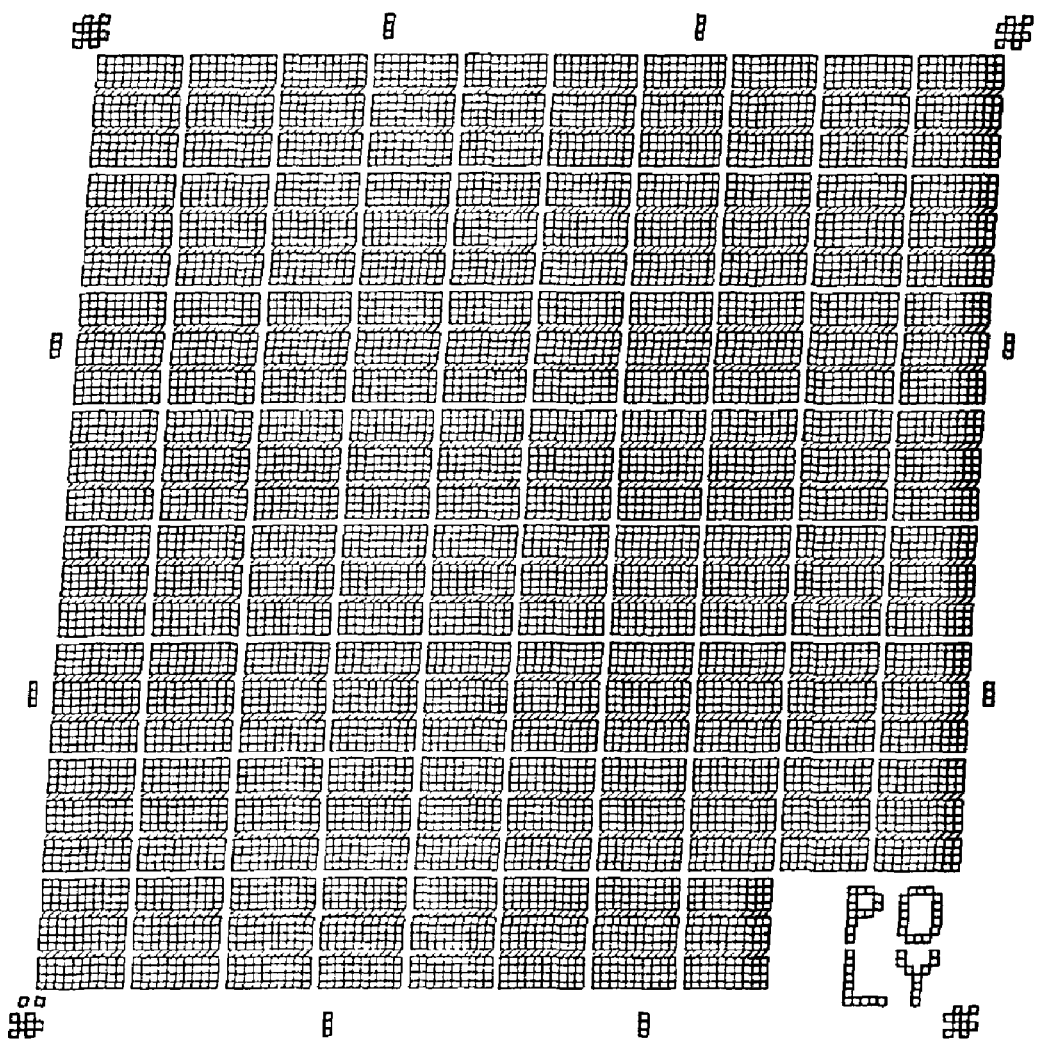
FIG. 2A shows a schematic representation of a single oligonucleotide array containing 78 separate detection blocks.
Figure 2B:
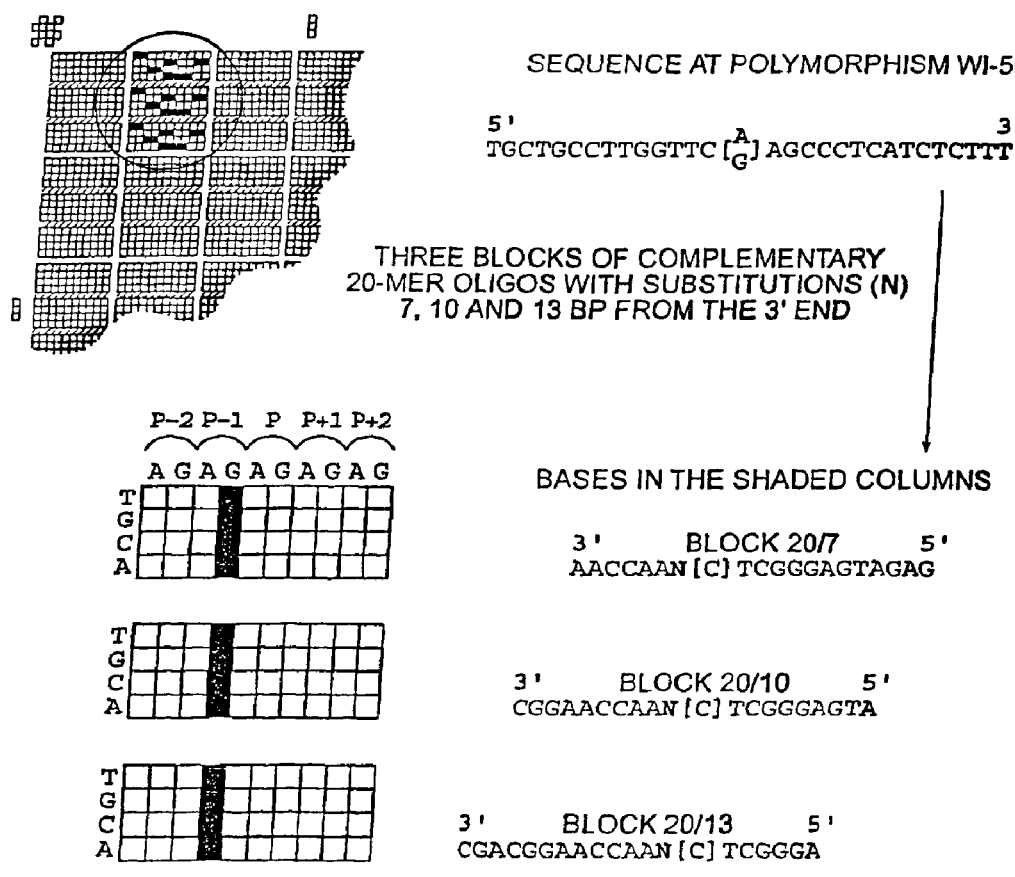
FIG. 2B shows a schematic illustration of a detection block for a specific polymorphism denoted WI-567 (TGCTGCCT-TGGT TCRAGCCCTCATCTCTTT, SEQ ID NO: 1).

A variety of tiling configurations may also be employed to ensure optimal discrimination of perfectly hybridizing probes. For example, a detection block may be tiled to provide probes having optimal hybridization intensities with minimal cross-hybridization. For example, where a sequence downstream from a polymorphic base is G-C rich, it could potentially give rise to a higher level of cross-hybridization or "noise," when analyzed. Accordingly, one can tile the detection block to take advantage of more of the upstream sequence. Such alternate tiling configurations are schematically illustrated in FIG. 2B, bottom, where the base in the probe that is complementary to the polymorphism is placed at different positions in the sequence of the probe relative to the 3' end of the probe. For ease of discussion, both the base which represents the polymorphism and the complementary base in the probe are referred to herein as the "polymorphic base" or "polymorphic marker."

Optimal tiling configurations may be determined for any particular polymorphism by comparative analysis. For example, triplet or larger detection blocks like those illustrated in FIG. 2B may be readily employed to select such optimal tiling strategies. Additionally, arrays will generally be tiled to provide for ease of reading and analysis. For example, the probes tiled within a detection block will generally be arranged so that reading across a detection block the probes are tiled in succession, i.e., progressing along the target sequence one or more base at a time (See, e.g., FIG. 3, middle).

Once an array is appropriately tiled for a given polymorphism or set of polymorphisms, the target nucleic acid is hybridized with the array and scanned. Hybridization and scanning are generally carried out by methods described in, e.g., Published PCT Application Nos. WO 92/10092 and WO 95/11995, and U.S. Pat. No. 5,424,186, previously incorporated herein by reference in their entirety for all purposes. In brief, a target nucleic acid sequence which includes one or more previously identified polymorphic markers is amplified by well known amplification techniques, e.g., PCR. Typically, this involves the use of primer sequences that are complementary to the two strands of the target sequence both upstream and downstream from the polymorphism. Asymmetric PCR techniques may also be used. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Although primarily described in terms of a single detection block, e.g., for detection of a single polymorphism, in preferred aspects, the arrays of the invention will include multiple detection blocks, and thus be capable of analyzing multiple, specific polymorphisms. For example, preferred arrays will generally include from about 50 to about 4000 different detection blocks with particularly preferred arrays including from 100 to 3000 different detection blocks.

In alternate arrangements, it will generally be understood that detection blocks may be grouped within a single array or in multiple, separate arrays so that varying, optimal conditions may be used during the hybridization of the target to the array. For example, it may often be desirable to provide for the detection of those polymorphisms that fall within G-C rich stretches of a genomic sequence, separately from those falling in A-T rich segments. This allows for the separate optimization of hybridization conditions for each situation.

IV. Calling

After hybridization and scanning, the hybridization data from the scanned array is then analyzed to identify which variant or variants of the polymorphic marker are present in the sample, or target sequence, as determined from the probes to which the target hybridized, i.e., one of the two homozygote forms or the heterozygote form. This determination is termed "calling" the genotype. Calling the genotype is typically a matter of comparing the hybridization data for each potential variant, and based upon that comparison, identifying the actual variant (for homozygotes) or variants (for heterozygotes) that are present. In one aspect, this comparison involves taking the ratio of hybridization intensities (corrected for average background levels) for the expected perfectly hybridizing probes for a first variant versus that of the second variant. Where the marker is homozygous for the first variant, this ratio will be a large number, theoretically approaching an infinite value. Where homozygous for the second variant, the ratio will be a very low number, i.e., theoretically approaching zero. Where the marker is heterozygous, the ratio will be approximately 1. These numbers are, as described, theoretical. Typically, the first ratio will be well in excess of 1, i.e., 2, 4, 5 or greater. Similarly, the second ratio will typically be substantially less than 1, i.e., 0 5, 0 2, 0 1 or less. The ratio for heterozygotes will typically be approximately equal to 1, i.e. from 0 7 to 1 5. These ratios can vary based upon the specific sequence surrounding the polymorphism, and can also be adjusted based upon a standard hybridization with a control sample containing the variants of the polymorphism.

The quality of a given call for a particular genotype may also be checked For example, the maximum perfect match intensity can be divided by a measure of the background noise (which may be represented by the standard deviation of the mismatched intensities). Where the ratio exceeds some preselected cut-off point, the call is determined to be good. For example, where the maximum intensity of the expected perfect matches exceeds twice the noise level, it might be termed a good call. In an additional aspect, the present invention provides software for performing the above described comparisons.

Figure 5:
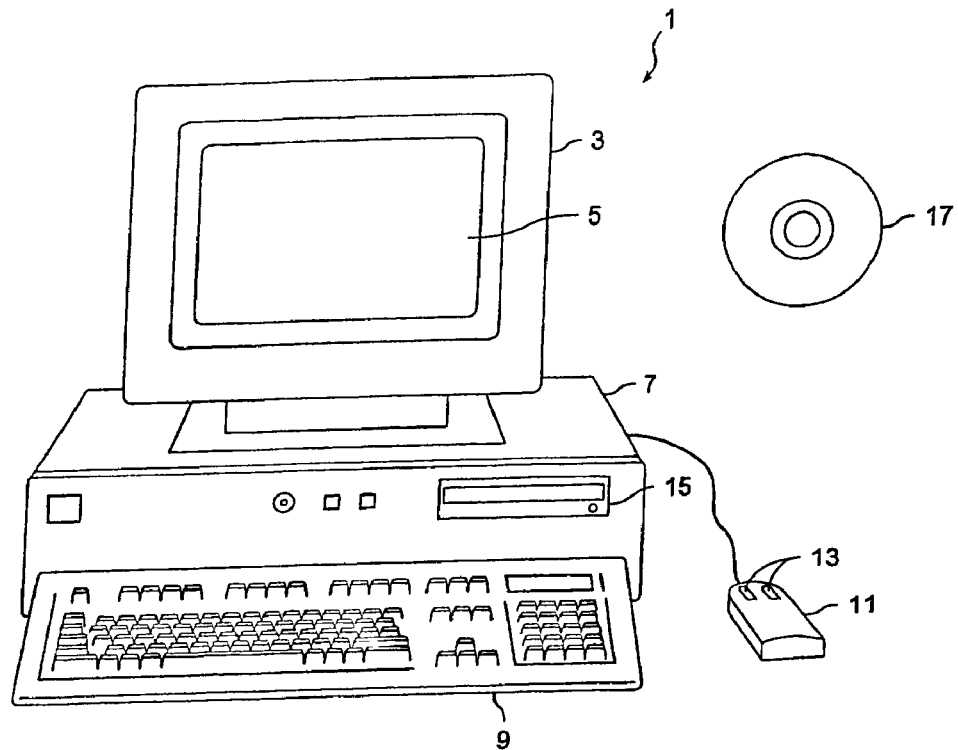
FIG. 5 illustrates an example of a computer system used to execute the software of the present invention which determines whether polymorphic markers in DNA are heterozygote, homozygote with a first polymorphic marker or homozygote with a second polymorphic marker.

FIG. 5 illustrates an example of a computer system used to execute the software of the present invention which determines whether polymorphic markers in DNA are heterozygote, homozygote with a first variant of a polymorphism or homozygote with a second variant of a polymorphism. FIG. 5 shows a computer system 1 which includes a monitor 3, screen 5, cabinet 7, keyboard 9, and mouse 11. Mouse 11 may have one or more buttons such as mouse buttons 13. Cabinet 7 houses a CD-ROM drive 15 or a hard drive (not shown) which may be utilized to store and retrieve software programs incorporating the present invention, digital images for use with the present invention, and the like. Although a CD-ROM 17 is shown as the removable media, other removable tangible media including floppy disks, tape, and flash memory may be utilized. Cabinet 7 also houses familiar computer components (not shown) such as a processor, memory, and the like.

Figure 6:
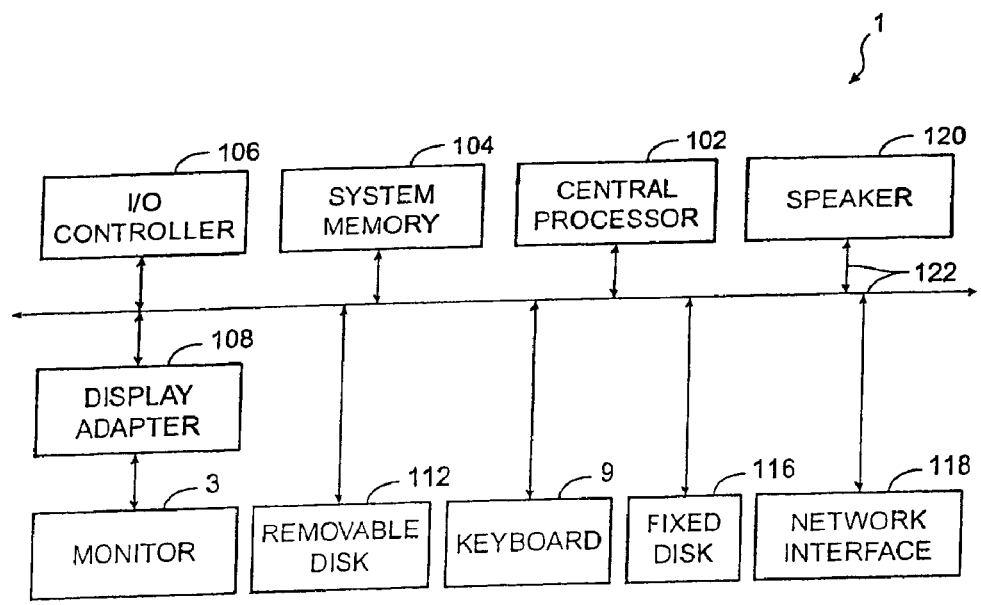
FIG. 6 shows a system block diagram of computer system 1 used to execute the software of the present invention.

FIG. 6 shows a system block diagram of computer system 1 used to execute the software of the present invention. As in FIG. 5, computer system 1 includes monitor 3 and keyboard 9. Computer system 1 further includes subsystems such as a central processor 102, system memory 104, I/O controller 106, display adapter 108, removable disk 112, fixed disk 116, network interface 118, and speaker 120. Other computer systems suitable for use with the present invention may include additional or fewer subsystems. For example, another computer system could include more than one processor 102 (i.e., a multi-processor system) or a cache memory.

Arrows such as 122 represent the system bus architecture of computer system 1. However, these arrows are illustrative of any interconnection scheme serving to link the Subsystems. For example, a local bus could be utilized to connect the central processor to the system memory and display adapter. Computer system 1 shown in FIG. 6 is but an example of a computer system suitable for use with the present invention. Other configurations of subsystems suitable for use with the present invention will be readily apparent to one of ordinary skill in the art.

Figure 7:
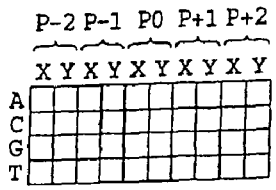
FIG. 7 shows a probe array including probes with base substitutions at base positions within two base positions of the polymorphic marker. The position of the polymorphic marker is denoted $P_0$ and which may have one of two polymorphic markers x and y (where x and y are one of A, C, G, or T).

FIG. 7 shows a probe array including probes with base substitutions at base positions within two base positions of the polymorphic marker. The position of the polymorphic marker is denoted $P_0$ and which may have one of two variants of the polymorphic markers x and y (where x and y are one of A, C, G, or T). As indicated, at $P_{-2}$ there are two columns of four cells which contain a base substitution two base positions to the left, or 3', from the polymorphic marker. The column denoted by an "x" contains polymorphic marker x and the column denoted by a "y" contains polymorphic marker y.

Similarly, $P_{-1}$ contains probes with base substitutions one base position to the left, or 3', of the polymorphic marker. $P_0$ contains probes with base substitutions at the polymorphic marker position. Accordingly, the two columns in $P_0$ are identical. $P_1$ and $P_2$ contain base substitutions one and two base positions to the right, or 5', of the polymorphic marker, respectively.

Figure 8:
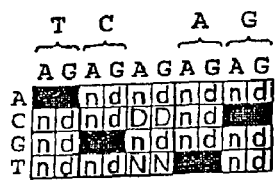
FIG. 8 shows a probe array including probes with base substitutions at base positions within two base positions of the polymorphic marker.

As a hypothetical example, assume a single base polymorphism exists where one allele contains the subsequence TC AAG whereas another allele contains the subsequence TC GAG, where the underlined base indicates the polymorphism in each allele. FIG. 8 shows a probe array including probes with base substitutions at base positions within two base positions of the polymorphic marker. In the first two columns, the cells which contain probes with base A (complementary to T in the alleles) two positions from the left of the polymorphic marker are shaded. They are shaded to indicate that it is expected that these cells would exhibit the highest hybridization to the labeled sample nucleic acid. Similarly, the second two columns have cells shaded which have probes with base G (complementary to C in the alleles) one position to the left of the polymorphic marker.

At the polymorphic marker position (corresponding to $P_0$ in FIG. 7), there are two columns; one denoted by an "A" and one denoted by a "G". Although, as indicated earlier, the probes in these two columns are identical, the probes contain base substitutions for the polymorphic marker position. An "N" indicates the cells that have probes which are expected to exhibit a strong hybridization if the allele contains a polymorphic marker A. As will become apparent in the following paragraphs, "N" stands for numerator because the intensity of these cells will be utilized in the numerator of an equation. Thus, the labels were chosen to aid the reader's understanding of the present invention.

A "D" indicates the cells that have probes which are expected to exhibit a strong hybridization if the allele contains a polymorphic marker G. "D" stands for denominator because the intensity of these cells will be utilized in the denominator of an equation. The "n" and "d" labeled cells indicate these cells contain probes with a single base mismatch near the polymorphic marker. As before, the labels indicate where the intensity of these cells will be utilized in a following equation.

Figure 9:
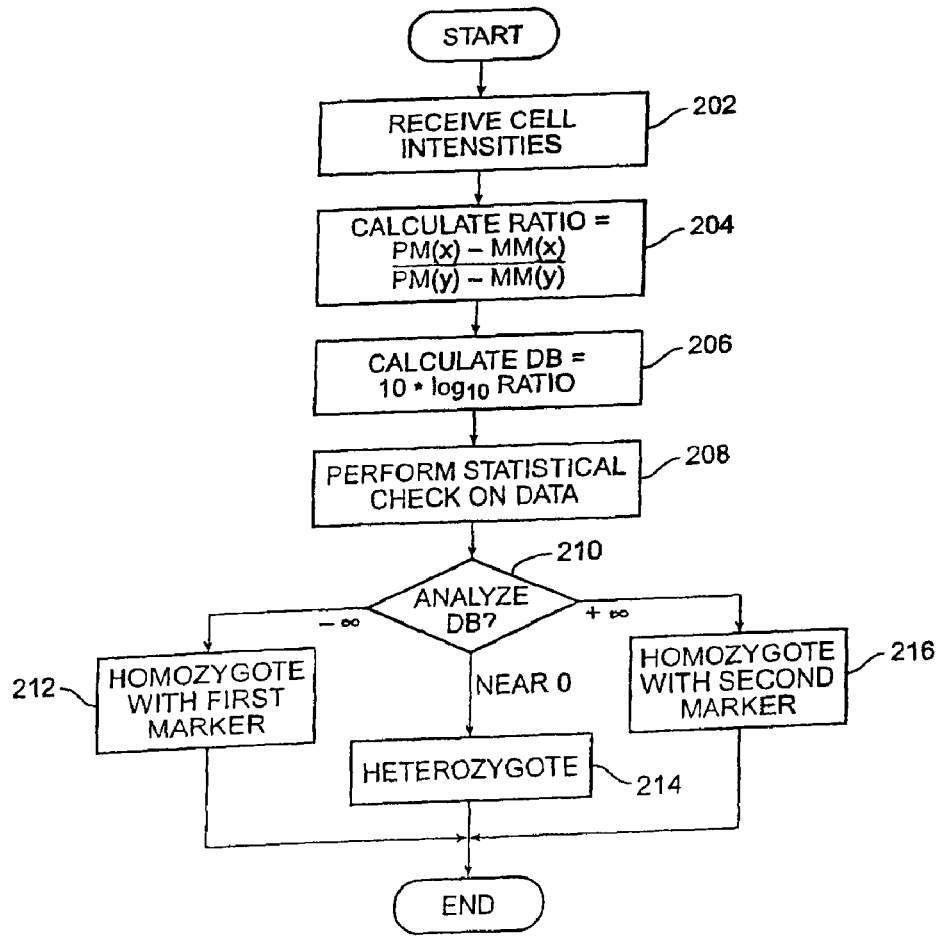
FIG. 9 shows a high level flowchart of analyzing intensities to determine whether polymorphic markers in DNA are heterozygote, homozygote with a first polymorphic marker or homozygote with a second polymorphic marker.

FIG. 9 shows a high level flowchart of analyzing intensities to determine whether polymorphic markers in DNA are heterozygote, homozygote with a first polymorphic marker or homozygote with a second polymorphic marker. At step 202, the system receives the fluorescent intensities of the cells on the chip. Although in a preferred embodiment, the hybridization of the probes to the sample are determined from fluorescent intensities, other methods and labels including radioactive labels may be utilized with the present invention. An example of one embodiment of a software program for carrying out this analysis is reprinted in Software Appendix A.

A perfect match (PM) average for a polymorphic marker x is determined by averaging the intensity of the cells at $P_0$ that have the base substitution equal to x an FIG. 7. Thus, for the example in FIG. 8, the perfect match average for A would add the intensities of the cells denoted by "N" and divide the sum by 2.

A mismatch (MM) average for a polymorphic marker x is determined by averaging the intensity of the cells that contain the polymorphic marker x and a single base mismatch in FIG. 7. Thus, for the example in FIG. 8, the mismatch average for A would be the sum of cells denoted by "n" and dividing the sum by 14.

A perfect match average and mismatch average for polymorphic marker y is determined in a similar manner utilizing the cells denoted by "D" and "d", respectively. Therefore, the perfect match averages are an average intensity of cells containing probes that are perfectly complementary to an allele. The mismatch averages are an average of intensity of cells containing probes that have a single base mismatch near the polymorphic marker in an allele.

At step 204, the system calculates a Ratio of the perfect match and mismatch averages for x to the perfect match and mismatch averages for y. The numerator of the Ratio includes the mismatch average for x subtracted from the perfect mismatch for x. In a preferred embodiment, if the resulting numerator is less than 0, the numerator is set equal to 0.

The denominator of the Ratio includes the mismatch average for y subtracted from the perfect mismatch for y. In a preferred embodiment, if the resulting denominator is less than or equal to 0, the numerator is set equal to a de minimum value like 0 00001.

Once the system has calculated the Ratio, the system calculates DB at step 206 DB is calculated by the equation $DB=10*\log_{10}Ratio$. The logarithmic function puts the ratio on a linear scale and makes at easier to interpret the results of the comparison of intensities.

At step 208, the system performs a statistical check on the data or hybridization intensities. The statistical check is performed to determine if the data will likely produce good results. In a preferred embodiment, the statistical check involves testing whether the maximum of the perfect match averages for x or y is at least twice as great as the standard deviation of the intensities of all the cells containing a single base mismatch (i.e., denoted by a "n" or "d" an FIG. 8). If the perfect match average is at least two times greater than this standard deviation, the data is likely to produce good results and this is communicated to the user.

The system analyzes DB at step 210 to determine if DB is approaching $-\infty$, near 0, or approaching $+\infty$. If DB is approaching a negative infinity, the system determines that the sample DNA contains a homozygote with a first polymorphic marker corresponding to x at step 212. If DB is near 0, the system determines that the sample DNA contains a heterozygote corresponding to both polymorphic markers x and y at step 214. Although described as approaching $\infty$, etc., as described previously, these numbers will generally vary, but are nonetheless indicative of the calls described. If DB is approaching a positive infinity, the system determines that the sample DNA contains a homozygote with a second polymorphic marker corresponding to y at step 216.

A visual inspection of the Ratio equation in step 204 shows that the numerator should be higher than the denominator if the DNA sample only has the polymorphic marker corresponding to x. Similarly, the denominator should be higher than the numerator if the DNA sample only has a polymorphic marker corresponding to y. If the DNA sample has both polymorphic markers, indicating a heterozygote, the Ratio should be approximately equal to 1 which results in a 0 when the logarithm of the Ratio is calculated.

The equations discussed above illustrate just one embodiment of the present invention. These equations have correctly identified polymorphic markers when a visual inspection would seem to indicate a different result. This may be the case because the equations take into account the mismatch intensities in order to determine the presence or absence of the polymorphic markers.

Those of skill in the art, upon reading the instant disclosure will appreciate that a variety of modifications to the above described methods and arrays may be made without departing from the spirit or scope of the invention. For example, one may select the strand of the target sequence to optimize the ability to call a particular genome. Alternatively, one may analyze both strands, in parallel, to provide greater amounts of data from which a call can be made. Additionally, the analyses, i.e., amplification and scanning may be performed using DNA, RNA, mixed polymers, and the like.

The present invention is further illustrated by the following examples. These examples are merely to illustrate aspects of the present invention and are not intended as limitations of this invention.

V. Examples

Example 1

Chip Tiling

A DNA chip is prepared which contains three detection blocks for each of 78 identified single base polymorphisms or biallelic markers, in a segment of human DNA (the "target" nucleic acid). Each detection block contains probes wherein the identified polymorphism occurs at the position in the target nucleic acid complementary to the 7th, 10th and 13th positions from the 3' end of 2O-mer oligonucleotide probes. A schematic representation of a single oligonucleotide array containing all 78 detection blocks is shown an FIG. 2A.

The tiling strategy for each block substitutes bases in the positions at, and up to two bases, in either direction from the polymorphism. In addition to the substituted positions, the oligonucleotides are synthesized in pairs differing at the biallelic base. Thus, the layout of the detection block (containing 40 different oligonucleotide probes) allows for controlled comparison of the sequences involved, as well as simple readout without need for complicated instrumentation. A schematic illustration of this tiling strategy within a single detection block is shown in FIG. 3, for a specific polymorphic marker denoted WI-567.

Example 2

Detection of Polymorphisms

A target nucleic acid is generated from PCR products amplified by primers flanking the markers. These amplicons can be produced singly or in multiplexed reactions. Target can be produced as ss-DNA by asymmetric PCR from one primer flanking the polymorphism or as RNA transcribed in vitro from promoters linked to the primers. Fluorescent label is introduced into target directly as dye-bearing nucleotides, or bound after amplification using dye-streptavidin complexes to incorporated biotin containing nucleotides. In DNA produced by asymmetric PCR fluorescent dye is linked directly to the 5' end of the primer.

Hybridization of target to the arrays tiled in Example 1, and subsequent washing are carried out with standard solutions of salt (SSPE, TMACl) and nonionic detergent (Triton-X1OO), with or without added organic solvent (formamide). Targets and markers generating strong signals are washed under stringent hybridization conditions (37-40° C.; 10% formamide; 0 25×SSPE washes) to give highly discriminating detection of the genotype. Markers giving lower hybridization intensity are washed under less stringent conditions ($\leq$30° C.; 3M TMACl, or 6×SSPE, 6× and 1×SSPE washes) to yield highly discriminating detection of the genotype.

Detection of one polymorphic marker is illustrated in FIG. 3. Specifically, a typical detection block is shown for the polymorphism denoted WI-1959, having the sequence 5'-ACCAAAAATCAGTC[T/C]GGGTAACTGAGAGTG-3' with the polymorphism indicated by the brackets (FIG. 3, top), for which all three genotypes are available (T/C heterozygote, C/C homozygote and T/T homozygote). The expected hybridization pattern for the homozygote and heterozygote targets are shown in FIG. 3, bottom. Three chips were tiled with each chip including the illustrated detection block. Each block contained probes having the substituted bases at the 7th, 10th and 13$^{th}$ positions from the 3' end of 20-mer oligonucleotide probes (20/7, 20/10 and 20/13, respectively). These alternate detection blocks were tiled to provide a variety of sequences flanking the polymorphism itself, to ensure at least one detection block hybridizing with a sufficiently low background intensity for adequate detection.

Fluorouracil containing RNA was synthesized from a T7 promoter on the upstream primer, hybridized to the detection array in 6×SSPE+Triton-X100 at 30° C., and washed in 0.25× SSPE at room temperature. As shown in the scan FIG. 3, middle, fluorescent scans of the arrays correctly identified the 5 homozygote or 10 heterozygote features.

Example 3

Alternate Gene Calling Method

An alternate method for calling the genotypes of a pedigree (or any collection of individuals) from P246 chip data is described herein. In particular, each sample from each of the individuals studied is amplified and hybridized to a P246 chip. The 246 chip employs a poly-tiling scheme and contains marker-specific control probes covering regions upstream and downstream from the single-base polymorphism. The significance of the control probes is that given that the target sample is amplified, these probes will display both perfect matches (PM) and single-base mismatches (MM) at known mismatch positions regardless of the target genotype. Even though in this document our description of the genotype calling method is based on the intensity data of a specific offset block (7/20, 10/20, 13/20) and a specific strand (T7, T3), this method is easily generalizable to accommodate data combining multiple offset blocks and strands.

Considering the data for a collection of individuals for a given marker and a given offset block and strand, the relevant raw data for each individual are (1) two control PM intensities, (2) the corresponding (mismatch position=offset) control MM intensities, (3) 40 block intensities, (4) interrogations for each of 2 alleles for each of 5 positions. The averages of the two control PMs and of the two control MMs are computed. The difference of the two averages (PM−MM) is labeled the Control Difference. For each of the 10 sets of 4 intensities (5 positions for each allele), the "possible" PM intensity is identified (Note that in individuals where the allele is present a PM will occur in a predetermined probe from the set of 4 interrogation probes, that probe is what we call "possible" PM). The hetero-MM probe (the same nucleotide appears at the mismatch position in both strands) is selected from the remaining 3, and the PM-MM difference is calculated. Each of the 10 block PM-MM values is divided by the Control Difference giving a Normalized Difference (ND). Thus the data for each individual are now reduced from 44 values to 10 ND values, 5 for each allele.

Figure 10:
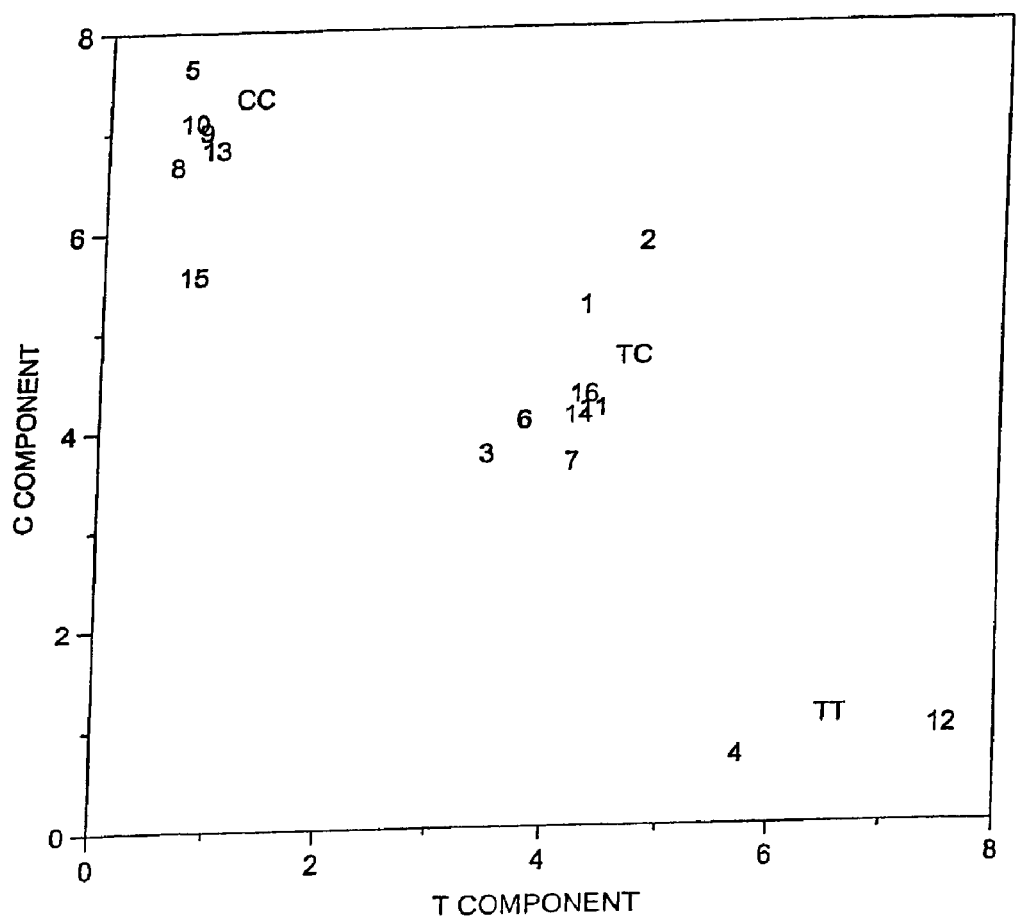
FIG. 10 shows a Principal Components Plot of Marker 219 (KRT8 m1).
Figure 11:
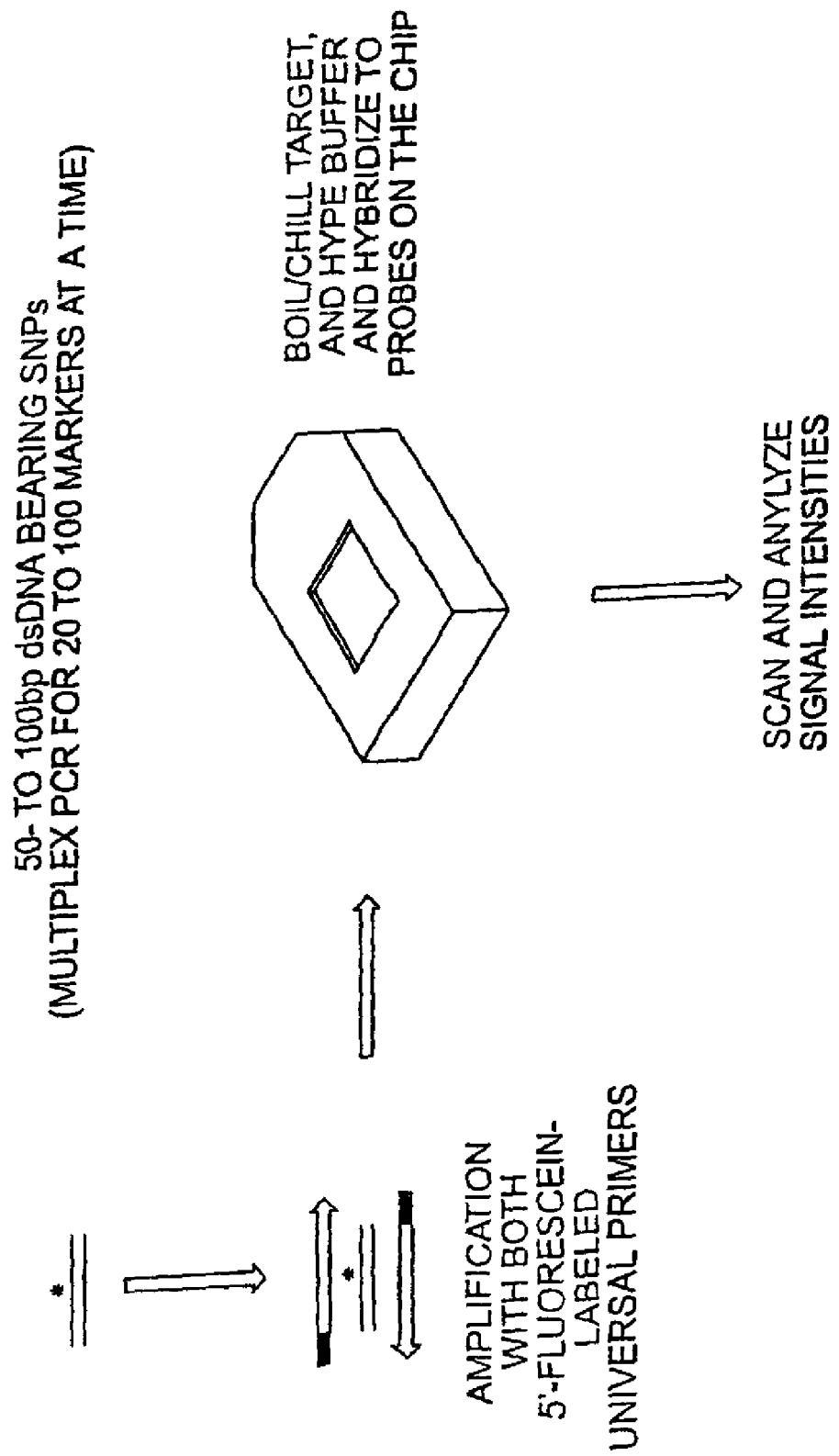
FIG. 11 shows a schematic representation of a process for carrying out the polymorphism detection methods of the invention.

Two principal components analyses (PCA) are then performed (see FIG. 10); one for each allele. PCA methodology originated with K Pearson (1901) *Philosophical Magazine*, 2, 559-572 as a means of fitting planes to data by orthogonal least squares, but was later proposed by Hotelling (1933) *Journal of Educational Psychology*, 26 417-441, 498-520 and Hotelling (1936) *Psychometrica*, 1:27-35. for the particular purpose of analyzing correlation structure. The correlation structure analyzed in our case is that of the 5 ND values correlated over individuals. PCA attempts to find hierarchical sets of coefficients so that the simple weighted average of the ND values using the first set of coefficients would account for the largest portion of the variability among individuals. The second set would account for the largest portion of remaining variability with the constraint that it is orthogonal (non-overlapping) to the first, and so on. Without being bound to a particular theory, it is believed that the major source of variability among individuals on the 5 ND scores is mainly due to the difference between those with the given allele and those without. Thus, it can be expected that the first principal component would capture this difference, so that the weighted average based on the first set of coefficients is computed, individuals with the allele will generally have high scores and those without will have low scores. Moreover, combining the PCA results from the two alleles will distinguish between homozygous individuals with the first allele (high PC scores on first low on second), homozygous individuals with the second allele (high PC scores on second low on first) and heterozygous individuals who will be high on both. This is illustrated in the enclosed plot of the two principal components for a set of 16 individuals from the K104 CEPH family. Clearly the individuals can be divided into three groups corresponding to the indicated genotypes.

Among the 221 biallelic markers detected on the polymorphism chip, seventeen of these markers were selected and assayed in a sixteen member CEPH family for genotyping by the present methods (see FIG. 14) and by ABI sequencing. Of the 272 genotypes called between the two methods, there were only three disagreements (~90% concordance). All the genotypes called by either method were consistent with Mendelian inheritance.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

APPENDIX A

SOFTWARE APPENDIX

```
( fullcal.awk )
( taxes input from a POLYcnsp CEL file (115 .times. 130) ans )
( extracts ratio information for every block on the chip )
BEGIN(
ratpatcutoff = 1.2
pattoggle = 'yes'
base (0) = "T"
base (1) = "G"
base (2) = "C"
base (3) = "A"
name(0.0) = 'WI-563'
hex(0.0) = 'TAGCC'
name(1.0) = 'WI-567'
hex(1.0) = 'TCAGAG'
name(2.0) = 'WI-597'
hex(2.0) = 'TGGATA'
name(3.0) = 'WI-681'
hex(3.0) = 'AACTAA'
name(4.0) = 'WI-801'
hex(4.0) = 'CTTGAG'
name(5.0) = 'WI-802'
hex(5.0) = 'CATCCT'
name(6.0) = 'WI-1099'
hex(6.0) = 'CAGATA'
```

APPENDIX A-continued

SOFTWARE APPENDIX

```
name(7.0) = 'WI-1147'
hex(7.0) = 'ACGAGC'
name(8.0) = 'WI-1325'
hex(8.0) = 'CTCTAC'
name(9.0) = 'WI-1417'
hex(9.0) = 'GTCTTT'
name(0.1) = 'WI-1736'
hex(0.1) = 'AAAGTC'
name(1.1) = 'WI-1825'
hex(1.1) = 'GTCTTC'
name(2.1) = 'WI-1879'
hex(2.1) = 'TACTCT'
name(3.1) = 'WI-1888'
hex(3.1) = 'ATGACA'
name(4.1) = 'WI-1912'
hex(4.1) = 'TTCTTT'
name(5.1) = 'WI-1959'
hex(5.1) = 'TCTCGG'
name(6.1) = 'WI-1741'
hex(6.1) = 'GAAGGC'
name(7.1) = 'WI-1760'
hex(7.1) = 'ACCACA'
name(8.1) = 'WI-1799'
hex(8.1) = 'TCGATA'
name(9.1) = 'WI-1973'
hex(9.1) = 'CAAGAG'
name(0.2) = 'WI-1980'
hex(0.2) = 'AACTGA'
name(1.2) = 'WI-2015'
hex(1.2) = ' GACTGT'
name(2.2) = 'WI-2664'
hex(2.2) = 'GGAGAG'
name(3.2) = 'WI-4013'
hex(3.2) = 'CTAGTG'
name(4.2) = 'WI-7567'
hex(4.2) = 'TAGTGA'
name(5.2) = 'WI-11595'
hex(5.2) = 'TAGAGC'
name(6.2) = 'CM4.16'
hex(6.2) = 'GATAAT'
name(7.2) = 'WI-6704'
hex(7.2) = 'ACTCCA'
name(8.2) = 'WI-6731'
hex(8.2) = 'GGCACA'
name(9.2) = 'WI-6787'
hex(9.2) = 'ACAGTT'
name(0.3) = 'WI-6910'
hex(0.3) = 'TAGTTG'
name(1.3) = 'WI-9518'
hex(1.3) = 'TTGATT'
name(2.3) = 'ADM-3'
hex(2.3) = 'ATAGTT'
name(3.3) = 'AGT'
hex(3.3) = 'TACTGG'
name(4.3) = 'ALDOB-1'
hex(4.3) = 'TTCTCG'
name(5.3) = 'ALDOB-2'
hex(5.3) = 'CCAGAT'
name(6.3) = 'APO3'
hex(6.3) = 'ACTCCT'
name(7.3) = 'APOE(152T/C)'
hex(7.3) = 'TGTCGC'
name(8.3) = 'APOE(290T/C)'
hex(8.3) = 'AGTCGC'
name(9.3) = 'AR88'
hex(9.3) = 'TCGATG'
name(0.4) = 'AT1a'
hex(0.4) = 'CTTCCC'
name(1.4) = 'AT1b'
hex(1.4) = 'GCACTT'
name(2.4) = 'BCL2'
hex(2.4) = 'ACGAGG'
name(3.4) = 'BRCA1a'
hex(3.4) = 'CATCTG'
name(4.4) = 'ERCA1b'
hex(4.4) = 'AGAGAG'
name(5.4) = 'ERCA1c'
hex(5.4) = 'GAAGAC'
```

APPENDIX A-continued

SOFTWARE APPENDIX

```
name(6.4) = 'D3S2'
hex(6.4) = 'CCAGGT'
name(7.4) = 'D3S11'
hex(7.4) = 'TCTGAA'
name(8.4) = 'D3S12'
hex(8.4) = 'CCAGGG'
name(9.4) = 'DRD2'
hex(9.4) = 'CACTGG'
name(0.5) = 'FABF2'
hex(0.5) = 'GCGACT'
name(1.5) = 'GCK'
hex(1.5) = 'GAGACA'
name(2.5) = 'NT2'
hex(2.5) = 'CTGTGG'
name(3.5) = 'HT2'
hex(3.5) = 'TGCAAT'
name(4.5) = 'HT4'
hex(4.5) = 'ACTCGA'
name(5.5) = 'HT5'
hex(5.5) = 'GGGACC'
name(6.5) = 'IGF2'
hex(6.5) = 'TCTCGA'
name(7.5) = 'IMS'
hex(7.5) = 'TCTACC'
name(8.5) = 'LDLA'
hex(8.5) = 'GGCTAA'
name(9.5) = 'LF79'
hex(9.5) = 'CCAGGG'
name(0.6) = 'LFL'
hex(0.6) = 'AGCTAG'
name(1.6) = 'NCC'
hex(1.6) = 'GCCTGA'
name(2.6) = 'METM'
hex(2.6) = 'CCCTGG'
name(3.6) = 'NEAMF'
hex(3.6) = 'CAGATG'
name(4.6) = 'FAR'
hex(4.6) = 'ACATTG'
name(5.6) = 'Per/RDS'
hex(5.6) = 'GAAGGA'
name(6.6) = 'PPP3R1'
hex(6.6) = 'GACTAA'
name(7.6) = 'RDS'
hex(7.6) = 'AGGACG'
name(8.6) = 's14544'
hex(8.6) = 'TCTGCT'
name(9.6) = '518CA'
hex(9.6) = 'GGCATG'
name(0.7) = 'TcA-CA1'
hex(0.7) = 'TGCGGT'
name(1.7) = 'TcR-CB22'
hex(1.7) = 'GGCTGG'
name(2.7) = 'TcR-CB23'
hex(2.7) = 'CTCTAG'
name(3.7) = 'TcR-CB24'
hex(3.7) = 'GTGATG'
name(4.7) = 'TcR-CB25'
hex(4.7) = 'GTAGCC'
name(5.7) = 'TcR-CB27'
hex(5.7) = 'ACCTTA'
name(6.7) = 'VB12a'
hex(6.7) = 'ACAGTG'
name(7.7) = 'VB12b'
hex(7.7) = 'CACTCA'
bxgsum = 0
bxgnum = 0
readthis = 1
if (S1 ~ /(A−Za−z)/ | S2 − /(A−Za−z1/) readthis = C
if (readthis == 1) rawdata/S1.S2) = S3
if (S1 > 2 && S2 > 4) if (S1 < 112 && S2 < 124) if (S1 < 90 .| S2 < 109)
  (
  px = int ((S1 − 3)/11)
  py = int ((S2 − 5)/15)
  pxo = (11*px) = 3
  pyo = (15*py) = 5
  mx = S1 − pxo
  by = S2 − pyo
  block = 3*(int(by/51) = 7 if (by%5 | = 4 == mx | = 10)
  (
  sb = base(by%5)
  sig(px,py,block,SD,mx) = S3
  )
if *by%5 == 4 || mx == 10)
  (
  bkgsum == S3
  bkgnum++
  )
  )
END(
printf ("background = %5.2f\n". bkgsum/bkgnum;
printf "MARKER\tEBSTBLK\tRATIO\t\tDB\tCHECK\t\tPATRAT\n")
for (py = 0, py < 8, py++, for (px = 0, px < 10, px++) if (py < 7 || px < 8)
  (
  m(0) = substrihex(px,py),1.1)
  m(1) = substrihex(px,py),1.1)
  m(2) = substrihex(px,py),2.1)
  m(3) = substrihex(px,py),2.1)
  m(4) = substrihex(px,py),3.2)
  m(5) = substrihex(px,py),3.2)
  m(6) = substrihex(px,py),5.1)
  m(7) = substrihex(px,py),5.1)
  m(8) = substrihex(px,py),6.1)
  m(9) = substrihex(px,py),6.1)
  center = substrihex(px,py),3.1)*/*substrihex(px,py),4.1)
  pantmer = m(0)**m(2)*("center")*m(6)**m(8)
  header = "('px + 1', 'py − 1')" name(px,py)) "\n* pentamer *\n"
  headprint = 0
  (
    for (j = 0;j <= 2; j++)
      (
      block = (3*j) + 7
      num2 = 0
      den2 = 0
      num1 = 0
      den1 = 0
      x2 = 0
      n1 = 0
      n2 = 0
      for (f = 0; f < 5; f++)
        (
        maxhi (px,py,block,f) = 0
        for (g = 0; g < 4; g++) maxio(px,py,black,g,f) = 0
      for (k = 0; k <= 4; k++) for (b = 0; b <= 3; b++)
        (
        z = int(k/2)
        signal = sig(px,py,block,bass(b),k)
        omit = 0
        if (mik) − bass(b)) omit = 1
        if (omit == 1)
          (
          q = maxhi (px,py,block,z)
          if (signal > q) maxni (px,py,block,b,z) = signal
          )
        if (omit == 0)
          (
          q = maxio (px,py,block,z)
          if (signal > q) maxio
            (px,py,block,b,z) = signal
          if (k42 == 0)
            (
            num2 == signal
            x2 == (signal) 2
            n1++
            )
          if (k42 == 1)
            (
            dan2 == signal
            x2 == (signal) 2
            n2++
            )
          )
          if (omit == 1) if (k == 4)/ k == 5,
            (
```

APPENDIX A-continued

SOFTWARE APPENDIX

```
  if (base(b) == substr(hex|px,py), 3.1))
    (
    num1 == signal
    )
  if (base(b) == substr(hex|px,pay), 4.1))
    (
    dan1 == signal
    )
    )
   )
  maxhisum == maxhi(px,py,block,f)
  )
 maxhisum = 0
 for (f = 0; f < 5; f++)
   (
 maxhisum = maxhisum/5
 maxiosum = 0
 for (g = 0; g < 5; g++) for (v = 0; v < 4; v,g)
   (
 maxiosum += maxio(px,py,block,v,g)
   )
maxiosv = maxiosum/14
maxrat = maxniav/maxioav
num = ((num1/2) − (num2/n1))
if (num < 0) num = 0
dan == 0 ((dan1/2) − (dan2/n2))
if (dan < 0) dan = 0.001
ratio = num/dan
max = num1/2
```

APPENDIX A-continued

SOFTWARE APPENDIX

```
if (dan1/2 < max1 max = dan1/2
n = n1 + n2
stdvxnum = ((n*x2) − (num2 + dan2)^2)
if (stdvxnum < 0) stdvx = 0
stdvx = (stdvxnum/(n^2))^(0.05)
if (maxrat > ratpatcutoff || pattoggle == 'no')
  (
  if (headprint == 0)
    (
    printf header
    headprint = 1
    )
  printf "\t20/"block"\t"
  printf ("%1.2f\t", ratio)
  if (ratio < 10000) printf "\t"
  rat = ratio
  if (ratio == 0) rat = .00001
  lograt = log(rat)/log(10)
  printf ("%2.2f\t", 10*lograt)
  printf ("%2.2f", max/stdvx)
  if (max/stdvx < 2) printf "\tFAIL\t"
  if (max/stdvx <= 2) printf "\t\t"
  printf ("%2.2f", maxrat)
  if (maxrat > ratpatcutoff) printf "\t*GOODFAT*"
  printf "\n"
  )
 )
)
```

---

What is claimed is:

1. A non-transitory computer-readable storage medium storing a computer-executable program product that determines a genotype of a sample of nucleic acid sequences, wherein the computer-executable program causes a computer to execute computer-executable code that comprises:

computer-executable code that receives a first hybridization intensity indicating hybridization affinity between a first set of probes and a first allele, the first set of probes being complementary to a portion of the first allele;

computer-executable code that receives a second hybridization intensity indicating hybridization affinity between a second set of probes and the first allele, the second set of probes having a single base mismatch with a portion of the first allele;

computer-executable code that calculates a first difference between the first and second hybridization intensities;

computer-executable code that receives a third hybridization intensity indicating hybridization affinity between a third set of probes and a second allele, the third set of probes being complementary to a portion of the second allele;

computer-executable code that receives a fourth hybridization intensity indicating hybridization affinity between a fourth set of probes and the second allele, the fourth set of probes having a single base mismatch with a portion of the second allele;

computer-executable code that calculates a second difference between the third and fourth hybridization intensities;

computer-executable code that compares the first and second differences to calculate a ratio of the first difference to the second difference; and computer-executable code that uses principal component analysis to compare the ratio to ratios calculated according to the same procedure as the ratio, calculated for each of a plurality of individuals in a population in order to determine the genotype of the sample of nucleic acid sequences.

2. The computer-readable storage medium of claim 1, wherein the computer-readable storage medium is memory, floppy disk, or CD-ROM.

3. The computer-readable medium of claim 2 wherein memory is flash memory.

4. The computer-readable medium of claim 2 wherein memory is tape memory.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO: 1:

TGCTGCCTTG GTTCRAGCCC TCATCTCTTT    30

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO: 2:

AACCAANCTC GGGAGTAGAG    20

(2) INFORMATION FOR SEQ ID NO: 3:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO: 3:

CGGAACCAAN CTCGGGAGTA                                           20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 4:

CGACGGAACC AANCTCGGGA                                           20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 5:

ACGGAACCAN GTTCGGGAGT                                           20

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 6:

ACGGAACCAN GCTCGGGAGT                                           20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 7:

CGGAACCAAN TTCGGGAGTA                                           20

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 8:

CGGAACCAAN CTCGGGAGTA                                           20

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 9:

GGAACCAAGN TCGGGAGTAG                                           20

```
(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 10:

GAACCAAGTN CGGGAGTAGA                                                   20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 11:

GAACCAAGCN CGGGAGTAGA                                                   20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

AACCAAGTTN GGGAGTAGAG                                                   20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 13:

AACCAAGCTN GGGAGTAGAG                                                   20

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO: 14:

ACCAAAAATC AGTCYGGGTA ACTGAGAGTG                                        30
```